United States Patent
Fischer et al.

(10) Patent No.: US 6,740,781 B2
(45) Date of Patent: May 25, 2004

(54) PROCESS FOR SEPARATING REACTION MIXTURES AND RECYCLING QUATERNARY SALTS AND BASES

(75) Inventors: Peter Fischer, Köln (DE); Sven Michael Hansen, Leverkusen (DE); Claus-Peter Reisinger, Wixom, MI (US)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/320,061

(22) Filed: Dec. 16, 2002

(65) Prior Publication Data

US 2003/0153779 A1 Aug. 14, 2003

(30) Foreign Application Priority Data

Dec. 27, 2001 (DE) .......................................... 101 64 143

(51) Int. Cl.[7] .............................. C07F 9/02; C07F 5/04; C07C 227/06
(52) U.S. Cl. ...................... 564/230; 564/281; 564/296; 568/9; 568/146; 568/286
(58) Field of Search ................................ 564/230, 281, 564/296; 568/9, 146, 286

(56) References Cited

U.S. PATENT DOCUMENTS

| | | | | |
|---|---|---|---|---|
| 3,227,748 A | * | 1/1966 | Bragdon et al. | 260/501 |
| 3,484,348 A | * | 12/1969 | Johnson et al. | 204/73 |
| 4,172,782 A | * | 10/1979 | Masuko et al. | 260/567.6 H |
| 4,349,485 A | | 9/1982 | Hallgren | 260/463 |
| 4,487,698 A | * | 12/1984 | Idel et al. | 210/639 |
| 5,231,210 A | | 7/1993 | Joyce et al. | 558/274 |
| 5,578,110 A | | 11/1996 | Nakasato et al. | 75/403 |
| 5,760,272 A | | 6/1998 | Pressman et al. | 558/274 |
| 5,898,079 A | | 4/1999 | Pressman et al. | 558/274 |
| 5,981,788 A | | 11/1999 | Ofori et al. | 558/274 |
| 6,310,232 B1 | | 10/2001 | Ofori et al. | 558/274 |

FOREIGN PATENT DOCUMENTS

| | | | | |
|---|---|---|---|---|
| EP | 0 763 521 A2 | * | 3/1997 | ......... C07C/211/62 |
| GB | 1 572 291 | | 7/1980 | |

* cited by examiner

*Primary Examiner*—Brian Davis
(74) *Attorney, Agent, or Firm*—Joseph C. Gil; Gary F. Matz; Aron Preis

(57) ABSTRACT

A process for the removal and recovery of quaternary salt (A) and base (D) from a reaction mixture is disclosed. The reaction mixture resulting from oxidative direct carbonylation contains in addition to (A) and (D), at least one hydroxyaromatic compound (B) and at least one reaction product (C) and optionally a solvent, and the process entails a) adding acid to the reaction mixture to cause conversion of (D) into a hydroxyaromatic compound (B2) b) separating the reaction mixture into b1.) that contains (C) and optionally (B) and/or (B2) and b2.) that contains (A) and optionally (B) and/or (B2), and c) reacting b1.) with a base (E) to re-form (D).

8 Claims, 6 Drawing Sheets

US 6,740,781 B2

PROCESS FOR SEPARATING REACTION MIXTURES AND RECYCLING QUATERNARY SALTS AND BASES

FIELD OF THE INVENTION

The present invention relates to a process recovery of catalyst components from a reaction mixture and particularly to reaction mixture from oxidative direct carbonylation.

SUMMARY OF THE INVENTION

A process for the removal and recovery of quaternary salt (A) and base (D) from a reaction mixture is disclosed. The reaction mixture resulting from oxidative direct carbonylation contains in addition to (A) and (D), at least one hydroxyaromatic compound (B) and at least one reaction product (C) and optionally a solvent, and the process entails
a) adding acid to the reaction mixture to cause conversion of (D) into a hydroxyaromatic compound (B2) b) separating the reaction mixture into b1.) that contains (C) and optionally (B) and/or (B2) and b2.) that contains (A) and optionally (B) and/or (B2), and c) reacting b1.) with a base (E) to re-form (D).

BACKGROUND OF THE INVENTION

During the oxidative direct carbonylation of aromatic hydroxy compounds in the presence of CO, $O_2$ a noble metal catalyst, preferably palladium, and also an inorganic cocatalyst (e.g. manganese, or cobalt salts), a base, a quaternary salt, various organic cocatalysts (e.g., quinones or hydroquinones) and drying agents are generally used (see e.g. DE-OS 27 38 437, U.S. Pat. No. 4,349,485, U.S. Pat. No. 5,231,210, EP-A 677 336, EP-A 858 991, U.S. Pat. No. 5,760,272). The process may be performed in a solvent.

After performing the reaction, product mixtures are obtained from these reactions which contain, inter alia, one or more quaternary salts A, a hydroxyaromatic compound B, reaction products C such as e.g. water and diaryl carbonates, a base D (incl. any being produced by deprotonation of a hydroxyaromatic compound with another base or the directly used salt of a hydroxyaromatic compound) and possibly solvent, additional catalyst components, auxiliary substances and impurities. Thus, there is the object of separating one or more products C from quaternary salts and bases (A and D), without decomposing sensitive products C and also recycling A, B and D to the reaction as quantitatively as possible without any of the impurities present in the reaction mixture.

The working-up of such streams in the absence of D, by an extraction and precipitation process, is disclosed in EP A1 913 197. However, this working-up process does not lead directly to re-useable products without impurities.

An extraction process for recovering bromide salts from reaction mixtures similar to those in the present application is disclosed in U.S. Pat. No. B 6,310,232. Here again, however, the process does not lead directly to re-useable products A, B and D.

DETAILED DESCRIPTION OF THE INVENTION

Figure 1:
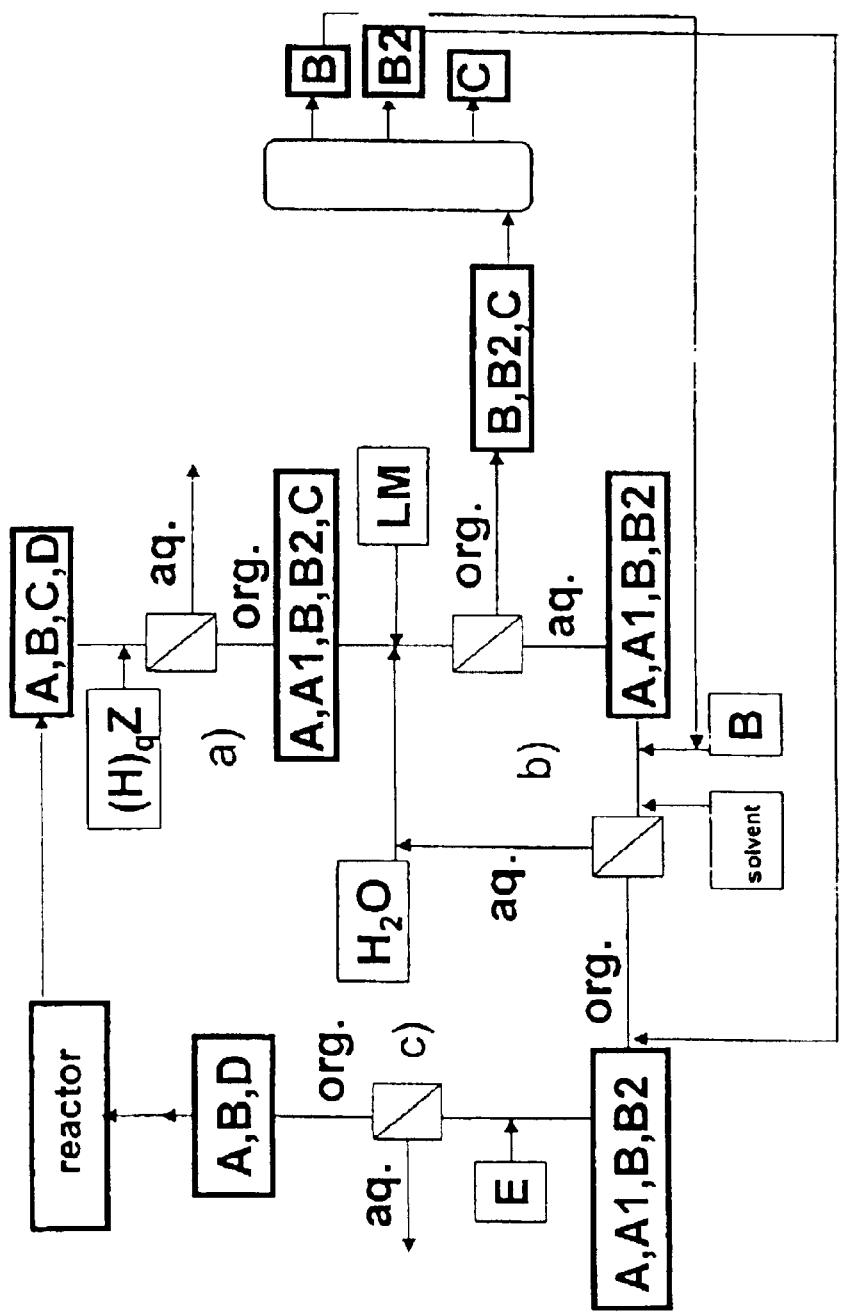
FIG. 1 shows a block diagram of the steps in an embodiment of the process of the present invention.

Surprisingly, during the detailed investigation of this problem, it was found that this object may be achieved by a suitable separation sequence that includes several specific individual steps.

Therefore, the invention provides a process for removing and recovering quaternary salts A of the formula $(Q^{n+})_m (Y^{m-})_n$, and bases D of the formula $(W^{l+})_k[(^-O)^k Ar']_l$, wherein n, m, k and l represent integers and Ar represents an aromatic group, from reaction mixtures which contain, in addition to A and D, at least hydroxyaromatic compounds B and reaction products C and optionally an inert solvent, characterized in that the following steps are performed:

a) the base D is converted into a hydroxyaromatic compound B2 by adding an acid $(H)_q Z$
b) a reaction mixture containing A, B, B2 and C and optionally an inert solvent is separated into mixtures which contain b1.) C and optionally B and/or B2 and b2.) A and optionally B and/or B2
c) a mixture of A, B and B2, e.g. b2.), is reacted with a base E, wherein D is formed again.

The separating process according to the invention is performed at a temperature of −10 to 250° C., preferably 10 to 130° C., particularly preferably 20 to 90° C., and at a pressure of 0.1 to 200 bar, preferably 0.5 to 50 bar, particularly preferably 1 to 10 bar, wherein the pressure and temperature may be varied over the individual steps.

The preferred inert organic solvent has a dielectric constant lower than about 20, particularly preferably solvents with dielectric constants less than about 15. The solvent has a boiling point of preferably between about 40 and about 200° C. The inert solvent may be present in the reaction mixture during reaction in a proportion of about 1 to 99%, preferably about 20 to 98%, particularly preferably about 40 to 95% relative to the total weight of the reaction mixture. The reaction mixture may optionally be concentrated before performing an individual sub-step by distilling off some of the solvent.

Hydrocarbons, halogenated hydrocarbons and aromatic solvents such as chlorobenzene, dichlorobenzene, fluorobenzene, benzene, toluene, anisol, cyclohexane, petroleum ether, methylene chloride or 1,2-dichloroethane, dipolar aprotic solvents such as dimethylacetamide, acetonitrile, N-methylpyrrolidone, ethers such as dioxan, tetrahydrofuran, t-butyl methyl ether and etherified glycols, optionally also mixtures of different solvents, may be used as solvents. Chlorobenzene is particularly preferably used.

Different solvents may be used for each of the individual steps a, b and c. However, use of the same solvent or solvent mixture for all the steps is preferred.

Aromatic hydroxy compounds B of the formula $Ar(OH)_p$, wherein p is an integer from 1 to 4 and Ar is an aromatic residue, which may be reacted in accordance with the invention are, for example, monohydroxy compounds (p=1)

such as phenol, o-, m- or p-cresol, o, m- or p-chlorophenol, o, m or p-ethylphenol, o-, m- or p-propylphenol, o, m, or p-tert-butylphenol, o, m or p-methoxyphenol, 2,6-dimethylphenol, 2,4-dimethyl-phenol, 3,4-dimethylphenol, 1-naphthol, 2-naphthol or dihydroxy (p=2) or polyhydroxy (p>2) compounds such as resorcinol and hydroquinone, as well as bisphenols such as 2,2-bis-(4-hydroxyphenyl)-propane, (bisphenol A), 2,2-bis-(3,5-dimethyl-4-hydroxyphenyl)-propane, 1,1-bis-(4-hydroxyphenyl)-cyclohexane, 1,1-bis-4-hydroxyphenyl)-3,3,5-trimethylcyclohexane or 6,6'-dihydroxy-3,3,3',3'-tetramethyl-1,1'-spiro(bis)-indane.

In general, in the event of substitution of the aromatic hydroxy compound, Ar may bear 1 to 4 substituents represented by $C_1$–$C_{18}$-alkyl, $C_6$–$C_{18}$-aryl, $C_7$–$C_{18}$-aralkyl, $C_1$–$C_4$-alkoxy, fluorine, chlorine or bromine. Mixtures of different aromatic hydroxy compounds may also be used. Monohydroxy compounds are preferably used, phenol being particularly preferred.

Quaternary salts A used within the scope of the present invention may be quaternary cations $Q^{n+}$, typically compounds of the formula $(XR_r^+)_n$, wherein X represents an atom from group VA or VIA, r is an integer between 0 and 4 and the Rs, independently of each other, represent $C_6$–$C_{18}$-aryl, $C_7$–$C_{18}$-aralkyl or $C_1$–$C_{20}$-alkyl groups.

In general, they are, for example, ammonium, guanidinium, phosphonium or sulfonium salts, substituted with organic groups, optionally also mixtures thereof. The letter n represents an integer. Oligomers (n>1) may also be used (in this case, (n−1) R-radicals form bridges between two Xs), but monomeric ions (n=1) are preferred. Ammonium, guanidinium, phosphonium, sulfonium and sulfoxonium ions, which contain $C_6$–$C_{18}$-aryl, $C_7$–$C_{18}$-aralkyl or $C_1$–$C_{18}$-alkyl groups as organic groups are suitable for use in the process according to the invention. The groups may be identical or different, optionally mixtures of several quaternary cations may also be used. Any pair of the substituent groups R may be replaced by a ring system.

The counterions, $Y^{m-}$, to the quaternary cations used may be e.g. halides, nitrates, sulfates, hydrogen sulfates, carbonates, hydrogen carbonates, phosphates, hydrogen phosphates, dihydrogen phosphates, tetrafluoroborates, carboxylates (preferably with $C_1$–$C_3$-alkyl chains such as e.g. formate or acetate), perchlorates or hexafluorophosphates. Mixtures of different anions are possible. The letter m represents an integer between 1 and 3.

Hexaalkylguanidinium halides, tetraalkylammonium halides and tetraarylphosphonium halides are preferred, tetrabutylammonium bromide, tetrabutyl ammonium chloride, tetraphenylphosphonium bromide and tetrabutylphosphonium bromide being particularly preferred. The amount of such a quaternary salt may be, for example, 0.01 to 30 wt. %, with respect to the weight of the reaction mixture. This amount is preferably 0.5 to 15 wt. %, particularly preferably 1 to 5 wt. %.

The base D is added in an amount which is independent of the stoichiometry. The ratio of platinum metal, e.g. palladium, to base is preferably chosen in such a way that 0.1 to 500, preferably 0.3 to 200, particularly preferably 0.9 to 130 equivalents of base are used per mole of platinum metal, e.g. palladium.

Bases which may be used for the process according to the invention are alkali metal hydroxides, alkali metal salts or quaternary salts of weak acids such as alkali metal tert-butylate or alkali metal salts or quaternary salts of aromatic hydroxy compounds of the formula $(W^{l+})_k[(^-O)_k Ar']_l$, where $Ar'(OH)_k$, wherein Ar' is defined in the same way as Ar above and k and l represent integers. An alkali metal salt or quaternary salt of the aromatic hydroxy compound which is defined by the choice of B, which should optionally also be converted into an organic carbonate, is very particularly preferably used, for example tetrabutyl ammonium or potassium phenolate.

The alkali metal salts (l=1) may be lithium, sodium, potassium, rubidium or caesium salts. The quaternary salts may be ammonium, phosphonium, pyridinium, sulfonium or guanidinium salts which contain $C_6$–$C_{18}$-aryl, $C_7$–$C_{18}$-aralkyl and/or $C_1$–$C_{20}$-alkyl groups as organic groups. The groups may be all identical or different, optionally mixtures of several quaternary salts may also be used. $W^{l+}$ therefore represents an alkali metal or quaternary cation of the type $Q^{n+}$, preferably lithium, sodium, potassium, hexaalkylguanidinium, tetraphenylphosphonium, tetrabutylammonium and tetrabutylphosphonium ions, particularly preferably sodium and tetrabutylammonium ions.

Even when other bases (e.g. hydroxides, carbonates or tertiary amines) are used as deprotonated hydroxy aromatic compounds of the type B (such as e.g. phenolates), a variable concentration of the deprotonated hydroxyaromatic compound $(W^{l+})_k[(^-O)_k Ar']_l$, is always produced at an intermediary stage due to the protonation equilibrium of the base with the compound B which is used to prepare C.

D is preferably selected so that the compound B2 produced therefrom in step a) is identical with B. Furthermore, the quaternary ions $Q^{n+}$ and $W^{l+}$ are preferably identical.

B2 therefore basically belongs to the group of hydroxy aromatic compounds defined under B, i.e. it is a compound of the formula (Ar')(OH)k, wherein k is an integer and (Ar'), defined as above, is an aromatic residue which is a member of the same group of aromatic residues as (Ar).

The process may be applied to a wide variety of reaction products C, although these are preferably sparingly soluble in water. Since, in the process according to the invention, the presence of hydroxyaromatic compounds is sometimes required, the process is most interesting for application to reaction products in which phenol or other hydroxyaromatic compounds are used as reactants, auxiliary substances, catalysts or other reaction components. The products of such reactions are therefore preferred.

Examples are etherifications, esterifications, substitution reactions, oxidations and reductions of hydroxyaromatic compounds. An example is the direct carbonylation of phenol, in which diphenyl carbonate is produced from carbon monoxide, oxygen and phenol. Therefore oligocarbonates or diaryl carbonates are preferred as product C, diphenyl carbonate being particularly preferred.

The reaction mixtures to be separated are characterized by the presence of solvent(s), one or more quaternary salts A, one or more bases D, a hydroxyaromatic compound B and one or more reaction products C. The reaction products C may sometimes also be undesired secondary products.

Such reaction mixtures occur, as mentioned, during the direct carbonylation of hydroxyaromatic compounds. In that case, product mixtures are obtained which typically contain solvent (e.g. chlorobenzene), phenol (B), diphenyl carbonate and secondary products (C), a phenolate base D (e.g. tetrabutylammonium phenolate) as well as impurities, secondary products, optionally also further catalyst components such as palladium compounds, compounds of the transition metal cocatalyst, its ligands, organic cocatalysts and other auxiliary substances.

In step a), an acid $(H)_q Z$ is added to the mixture which contains A, B, C and D, wherein D reacts to give B2 and a quaternary salt of the formula $(W^{l+})_s([(H)_{q-s}Z]^{s-})_l$, is produced, this being called A1 in the following.

$([(H)_{q-s}Z]^{s-})_l$ is preferably identical to $(Y^{m-})_n$, i.e. also l=n and m=s. Furthermore, the quaternary ions $Q^{n+}$ and $W^{l+}$ are preferably identical. If both these conditions are satisfied, A1 is identical to A.

The stoichiometry of $(H)_qZ$ with respect to D is preferably about 0.95 to 3 equivalents. (Depending on the acid strengths for the individual dissociation steps of polybasic acids (q>1) relative to the basicity of D and the desired $([(H)_{q-s}Z]^{s-})$, one or more steps are used to calculate the equivalents. For example, sulfuric acid solutions (q=2) react to give both $(W^{l+})_2(SO_4)_l$ (s=2) and also $(W^{l+})(HSO_4)_l$ (s=1). (However, at least the first dissociation step should have a higher dissociation constant than that of B2).

Instead of $(H)_qZ$ their anhydrides, i.e. $(H)_qZ$ minus $H_2O$ (like e.g. acetic anhydride, $CO_2$ or $SO_3$) or similar precursor compounds may be used.

Acids such as $CO_2$, which in situ produces the salts of the acid $H_2CO_3$ may readily be removed from the reaction mixture, e.g. by gas stripping, may also be used in a substantially higher excess without causing problems.

The acid $(H)_qZ$ (q represents an integer) may be added, for example, as an aqueous solution, a solid, a liquid or a gas. Addition as an aqueous solution is preferred.

Examples of $(H)_qZ$ which may be added as gases are e.g. $CO_2$, $SO_3$, $SO_2$, HCl or HBr. HBr is preferred. The gases are added to the reaction mixture at a pressure higher than the reaction pressure using a suitable mixing device, e.g. nozzles or bubble chambers.

Examples of $(H)_qZ$ which may be added as solids are e.g. dry ice, oxalic acid, glacial acetic acid, potassium hydrogen sulfate, potassium dihydrogen phosphate, phosphoric acid. The solid, provided it is not transformed directly into another state of aggregation under the conditions mentioned, is added in as fine as possible a powdered form.

Examples of liquid $(H)_qZ$ which may be added are approximately 100% strength acids such as hydrobromic acid, sulfuric acid, nitric acid, phosphoric acid, formic acid, acetic acid. Hydrobromic acid is preferred. In the case of oxidising acids $(H)_qZ$ such as sulfuric or nitric acid, however, addition in this form is generally inappropriate in most cases. The liquids are added using a suitable mixing device.

Examples of aqueous solutions of $(H)_qZ$ are sulfuric acid, nitric acid, phosphoric acid, carbon dioxide, hydrochloric acid, hydrobromic acid, hydroiodic acid, aqueous formic acid, aqueous acetic acid, aqueous oxalic acid, aqueous citric acid. Hydrobromic, sulfuric, phosphoric and hydrochloric acids are preferred, hydrobromic acid being particularly preferred.

Preferred, particularly preferred or very particularly preferred etc. embodiments are those which make use of the parameters, compounds, definitions and explanations mentioned under preferred, particularly preferred or very particularly preferred.

The definitions, parameters, compounds and explanations specified above in general or specified in preferred ranges, however may also be combined with each other in any way, that is between the respective ranges and preferred ranges.

Contact with the reaction mixture is made using suitable mixing devices. The aqueous solution is preferably then separated before performing step b). In this case, step a) may be regarded as a reactive extraction and be performed in apparatus suitable for that purpose such as mixer-settlers or extraction columns or cascades of one or more of these elements. Step a) is preferably performed in an individual mixer-settler.

In the case of a reactive extraction, the ratio of aqueous phase to organic phase is generally held at such a level that the loss of A in the aqueous phase is restricted, but adequate contact between the reactants is ensured. A ratio by volume of aqueous to organic phases of 0.8 to 0.01 is preferred, particularly preferably 0.25 to 0.03, very particularly preferably 0.15 to 0.05. The contact time between the phases required is simple to determine by a person skilled in the art, but is, for example, about 2 seconds to 30 minutes.

The ratio of equivalents of $(H)_qZ$ to D is preferably 0.95 to 3, particularly preferably 1.03 to 2, because an excess of acid or the likewise preferred addition of another electrolyte minimizes the loss of A in the aqueous phase.

When performing a) by extraction, it was demonstrated that the metallic cocatalyst component present could be almost completely removed.

The application therefore also provides a process for the simultaneous neutralization of a base D and separation of one or more metal salts by reactive extraction of an organic solution which contains at least B, C and D, with an aqueous acid solution, wherein an organic phase which contains B2 and an aqueous phase which contains a metal salt are produced.

B, C and D and the solvent are defined in the same way as already mentioned above. The metal salt may be, for example, a metal from the groups IIIA, IIIB, IVA, IVB, VB, IB, IIB, VIB, VIIB, the rare earth metals (atomic numbers 58–71) or the iron group in the Periodic System of Elements (Mendeleev), optionally also mixtures thereof, wherein the metal may be used in different oxidation states (see e.g. U.S. Pat. No. 5,142,086, U.S. Pat. No. 5,231,210, U.S. Pat. No. 5,284,964, EP-A 350697, EP-A 350700, U.S. Pat. No. 5,336,803). Pb, Ti, Mn, Cu, Co, V, Zn, Ce and Mo are preferably used. Without restricting the process according to the invention, lead(II), manganese(II), manganese(III), copper(I), copper(II), cobalt(II), cobalt(III), vanadium (III) and vanadium(IV) may be mentioned.

Mn, Cu, Mo, Pb and Ce are particularly preferably used.

The metals may be used, for example, as halides, oxides, carboxylates of $C_2$–$C_{18}$-carboxylic acids, diketonates or nitrates as well as complex compounds which may contain, for example, carbon monoxide, olefins, aromatic and aliphatic monoamines or polyamines, phosphorus compounds, pyridines, bipyridines, terpyridines, quinolines, isoquinolines, cryptands, Schiff's bases and halides.

Manganese compounds are very particularly preferred in the process according to the invention, in particular manganese(II) and manganese(III) salts, especially as acetylacetonate complexes or halides, and as halogeno or mixed complexes, ideally as manganese(II) bromide.

The concentration of the metal salt is generally in the range 0.0001 to 20 wt. % of the reaction mixture, the concentration range preferably being 0.001 to 5 wt. %, particularly preferably 0.005 to 2 wt. %.

The metal salt may then be worked up and recovered from the aqueous phase in an appropriate manner. Processes which are known to a person skilled in the art such as crystallization from concentrated solutions, evaporating to dryness, extraction or precipitation may be used, for example.

In step b) the reaction mixture which contains the mixture of A, A1, B, B2 and C and optionally solvent is separated into mixtures which contain b1.) C and optionally B and/or B2 and b2.) A and optionally A1 and optionally B and/or B2.

The process according to the invention has the advantage that, after performing a), no more basic components are added which might lead to problematic secondary reactions, e.g. the saponification of diaryl carbonates, when separating C in step b). Thus, it is also possible to perform e.g. distillations at elevated temperature without losing C.

Step b) is preferably performed by distillation or extraction or combinations and/or cascades of the two, particularly preferably by extraction.

When performing step b) by distillation, the product C is distilled off via the head, generally after optional removal of the solvent by distillation, and A and A1 remain in the bottom container. Depending on the volatility, B or B2 accumulates in the bottom container or in the distillate or may optionally be obtained in enriched fractions by fractional distillation. For example, when working-up diphenyl carbonate (C), phenol (B) and optionally B2 are found in the most volatile fraction, diphenyl carbonate is found in the middle fraction and A and A1, optionally B2 and high-boiling impurities, remain in the bottom container and these latter may be separated from A and A1 in a separate step in the bottom container or in a sub-stream therefrom.

The bottom container contains A and A1 in liquid or solid form and these may be recycled to the reaction, optionally after dilution with B or solvents and/or further working-up steps.

Since the quaternary salts A and A1 are generally not very thermally stable, distillation is preferably performed at a temperature which is somewhat below the decomposition temperature and under as high a vacuum as possible. In the case of barely volatile products C, thermally stable quaternary salts should be used or another processing method should be applied.

Distillation may be performed in equipment which is familiar to a person skilled in the art.

The preferred embodiment of step b) is extraction or a sequence of extraction steps.

Another variant for performing step b) is the depletion of C by crystallisation of C or adducts or mixed crystals of C and B. The crystallisate may be used to separate C (fraction b1); the mother liquor (b2) which contains A and A1 and residual amounts of C may be recycled to the reaction.

When performing the direct carbonylation process, it is sensible to recycle the hydroxyaromatic compounds B and B2 to the reaction. If, in step b), the product C is produced as a mixture with B or B2 in fraction b1.) then it is sensible to perform another separating step to separate C and the hydroxyaromatic compounds B/B2. Distillation or crystallisation of C, for example, may be suitable for this purpose (see e.g., EP A1 801 053). The streams which are highly enriched with B and/or B2 and depleted in C which are produced thereby may optionally be combined with the fraction b2.), which contains A, produced in step b) and the mixture produced in this way may be used in step c). Alternatively these streams may be recycled directly to the reaction.

In step c), the fraction of reaction mixture which contains A, A1, B and B2 is reacted with a base E, wherein A1 and B2 react to give D. The base may be added in solid or liquid form or as an aqueous solution. Aqueous solutions are preferred.

The base E contains one or more members of the group consisting of alkaline earth metal, alkali metal and ammonium or quaternary salt $(Q^{n+})$ hydroxides. The quaternary salt may optionally be bonded as a polymer, e.g. in the form of an anion exchanger.

Examples of suitable bases E are also trialkylamines such as tributylamine, diisopropylethylamine, DBU, DBN. Anion exchangers such as Lewatit MP 62, MP 64 or VP OC 1072 and the hydroxides of the elements of groups IA and IIA in the Periodic System of Elements are preferred. Calcium hydroxide and potassium hydroxide are particularly preferred and sodium hydroxide is very particularly preferred.

If the base E is added as a solid, it should be added in the finest possible powdered form. The use of suitable $(Q^{n+})_m$ $(Y^{m-})_n$ or crown ethers or cryptands as phase transfer catalysts may accelerate the reaction.

Step c) is preferably performed by reactive distillation or reactive extraction or combinations of the two, particularly preferably by reactive extraction.

Reactive distillation may be performed in equipment which is known to a person skilled in the art.

Steps a), b) and c) in the present invention may each be performed as individual, multiple or continuous separating operations. Continuous processes, e.g. counterstream extraction are generally preferred.

For steps a), b) and c) in the process according to the invention, extraction processes, for example, may be used, such as are described for example in KIRK-OTHMER, Encyclopedia of Chemical Technology, fourth edition, volume 10, 1993, pages 125–181 and in Ullmann's Encyclopedia of Industrial Chemistry, fifth edition, volume B3, Unit Operations II, 1988, chapter 6, Liquid-Liquid Extraction, pages 6–1 to 6–61.

To perform the process according to the invention, extraction equipment of the following types may be used, such as e.g. columns with no energy input, columns with pulsed liquid or pulsed baffles, columns with rotating baffles, mixer-settlers, mixing nozzles and sedimentation tanks, as well as centrifugal extractors.

Examples of columns with no energy input which may be mentioned are spray columns, packed columns and perforated plate columns, which differ in the mode of dispersion of the phases.

Examples of columns with pulsed liquid or pulsed baffles which may be mentioned are pulsed perforated plate columns, with piston pumps, with Misek or Wepuko pulsators, columns with Prochazka or Karr vibrating perforated plates.

Examples of columns with rotating baffles which may be mentioned are rotating disc contactors (RDC), asymmetric rotating disc extractors (ARD), Oldshue-Rushton multiple-mixer columns, Kuhni extractors, Scheibel columns, SHE extractors and Graesser contactors.

Examples of mixer-settlers which may be mentioned are Davy-McKee mixer-settlers, Lurgi tower extractors, IMI, General Mills and Boxtyp Denver mixer-settlers.

Examples of centrifugal extractors which may be mentioned are Podbielniak centrifugal extractors and Rotabel centrifugal extractors.

The extractors may be operated as individual extractors, parallel extractors or as cascades of extractors. When using cascades of extraction equipment, equipment from one or different groups may be used simultaneously in the same cascade. Management of the phases may be performed in co-current or, preferably, in countercurrent in one cascade.

FIGS. 1 to 6 show embodiments of the process, which are intended to illustrate the possible variants without restricting the process in any way at all.

In FIG. 1, the mixture of quaternary salt A, hydroxy aromatic compound B, reaction product C and base D emerging from the reactor is extracted with an aqueous acid solution $(H)_qZ$ in step a), wherein D and $(H)_qZ$ are converted to B2 and A1. The products remain in the organic phase which is then subjected to step b). Step b) is characterized here in that water is passed round a circuit in the extraction process, which may minimise the amount of waste water.

The mixture is first diluted with solvent, then extracted with water. An aqueous phase is produced which contains A, A1 and the two hydroxy aromatic compounds and also an organic phase consisting of the product B, B2 and C. The organic solvent is worked-up here using, optionally multi-stage, fractional distillation. The reaction product C is taken off as the middle fraction, B and B2 are recovered separately or together as the most volatile products. B is recycled to step b), where solvent and B are added to the aqueous phase and the mixture is extracted. Due to the high proportion of B, A and A1 (together with B and B2) may be extracted in the organic phase; the aqueous phase contains only a little B or B2 and may be used again in the first extraction step. Base E is added to the mixture of A, A1, B and B2 and A1 and B2 are reconverted to give D in a reactive extraction process; A, B and D remain in the organic phase and are recycled to the reactor, optionally after further working-up or purification steps, e.g. removal of secondary products or drying.

Figure 2:
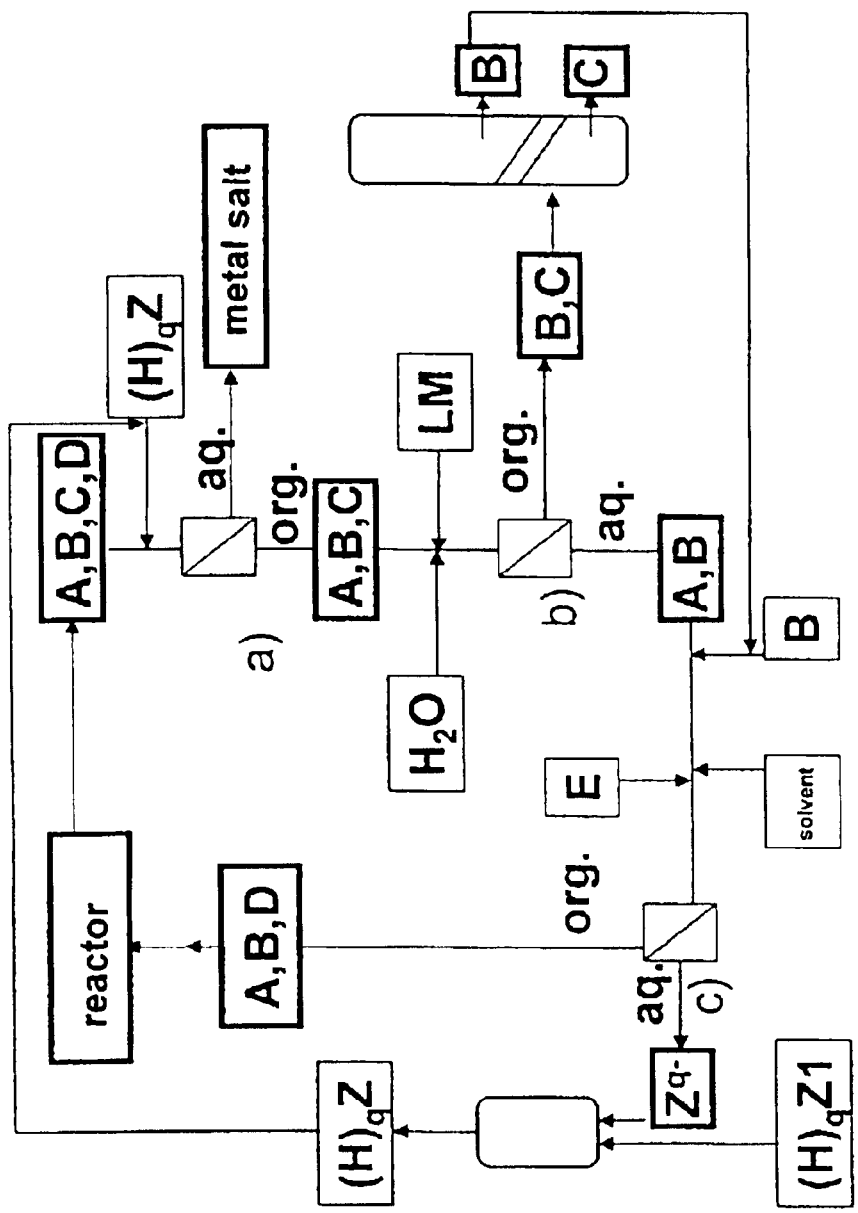
FIG. 2 shows a block diagram of the steps in an embodiment of the process of the present invention.

In FIG. 2, step a) is performed in the same way. The aqueous solution which contains a metal salt from the catalyst system may be worked-up to recover the metal salt. In this example, D is chosen in such a way that the B2 being produced by neutralisation is identical to B and A1 is identical to A. The mixture of A, B and C in the organic phase is then optionally diluted with solvent, water is added and an extraction is performed. An aqueous phase is produced which consists of A and a little B, as well as an organic phase with B and C. The mixture of B and C in this example is crystallised. The product C remains in the crystallisate; B and traces of C accumulate in the mother liquor. This stream is used to supplement the amount of B in step c) where the aqueous phase is diluted with solvent, E is added and an extraction is performed. The organic phase then contains A, B and D and is recycled to the reactor, optionally after working-up or purification steps, e.g. removal of secondary products or drying.

The acid anion $Z^{q-}$ is found in the aqueous phase and this may be reacted with another acid $(H)_wZ1$, where w represents an integer, in order to regenerate $(H)_qZ$ for step a). $(H)_qZ$ is thus circulated here.

Such circulation of $(H)_qZ$ is sensible when expensive acids are used. One possible variant is e.g. that A is a tetrabutylammonium bromide, and D is a tetrabutylammonium phenolate. If $(H)_qZ$ is hydrobromic acid, tetrabutylammonium bromide is produced in step a) and bromide $(Z^{q-})$ is eliminated in step c). The valuable substance bromide may be reconverted into hydrobromic acid by adding inexpensive sulfuric acid $((H)_wZ1)$ to the aqueous solution and distilling, wherein an aqueous HBr solution is obtained which may then be used again in step a).

One variant of this process separates some of the $Z^{q-}$ from water, e.g. by reverse osmosis or distillation, after step c), and thus enables recycling of a water stream as the feed for step b).

Figure 3:
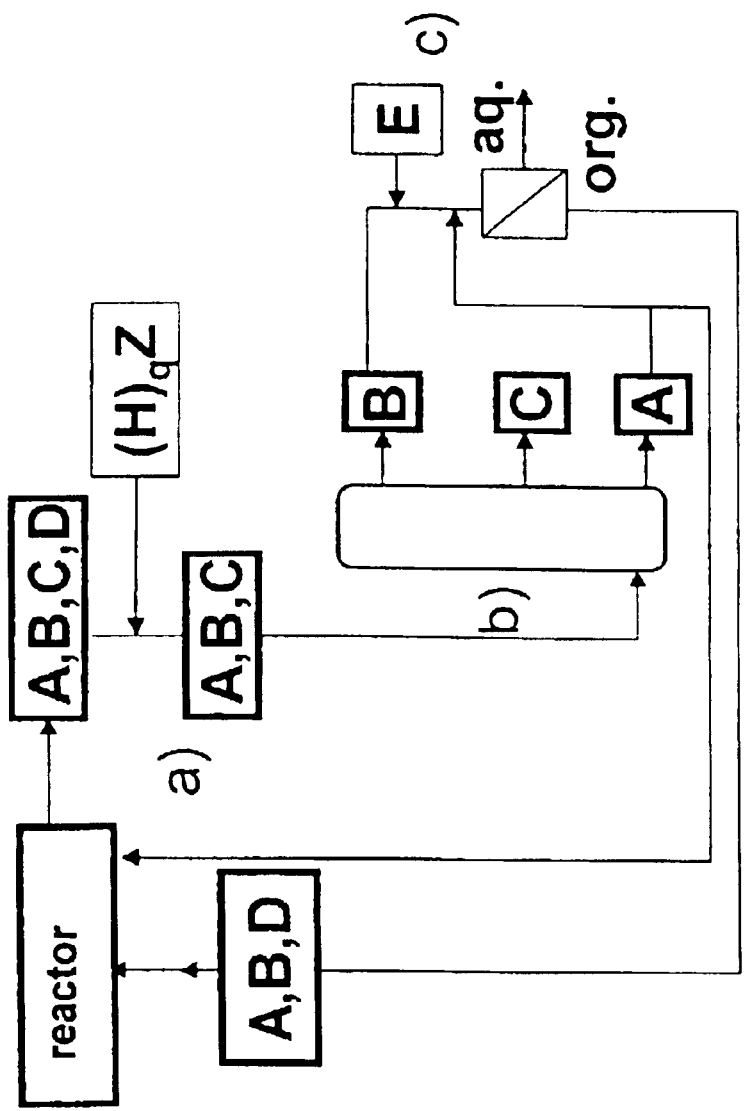
FIG. 3 shows a block diagram of the steps in an embodiment of the process of the present invention.

FIG. 3 shows a variant in which the acid is added as such in solid or liquid form (or dissolved in a solvent). In this example D was chosen in such a way that the B2 being produced by neutralisation is identical to B and A1 is identical to A. In step b), the mixture of A, B and C is separated by fractional distillation. A remains in the container at the base of the column, is dissolved in a backstream of B and is recycled to the reaction, optionally after working-up or purification steps, e.g. removal of secondary products or drying. Some of the B which is distilled off is used for step c), where D is produced in a reactive extraction. D is dissolved in a back-stream of B and recycled to the reactor.

Figure 4:
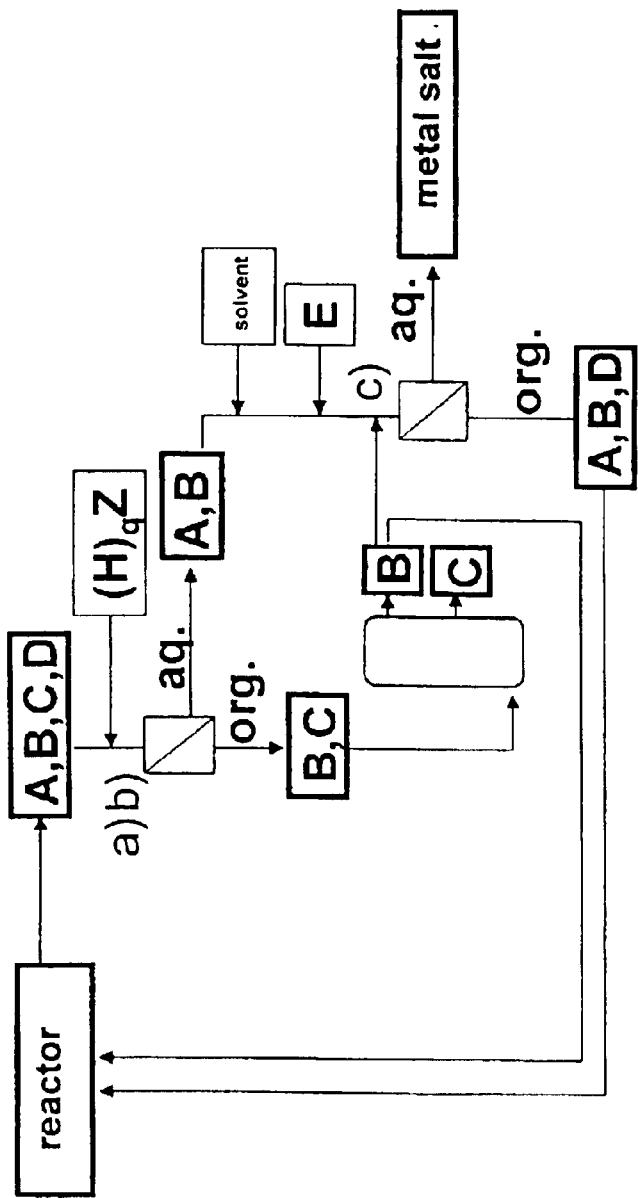
FIG. 4 shows a block diagram of the steps in an embodiment of the process of the present invention.

FIG. 4 shows an example in which D was again chosen in such a way that the B2 being produced by neutralisation is identical to B and A1 is identical to A. This is a variant in which step a) is performed with a large aqueous/organic phase ratio and exact stoichiometry. If this extraction is performed as a multi-stage process, step b) may be incorporated into this extraction. An organic phase which contains B and C, and is e.g. split into the components by distillation, is obtained and an aqueous phase consisting of A and B are obtained. D is produced therefrom by partial reaction in a reactive extraction (step c)) and the mixture of A, B and D, as well as pure B, is recycled to the reaction. The aqueous phase present in step c) optionally contains one or more metal salts from catalyst components and may be worked-up to regenerate these metals.

Figure 5:
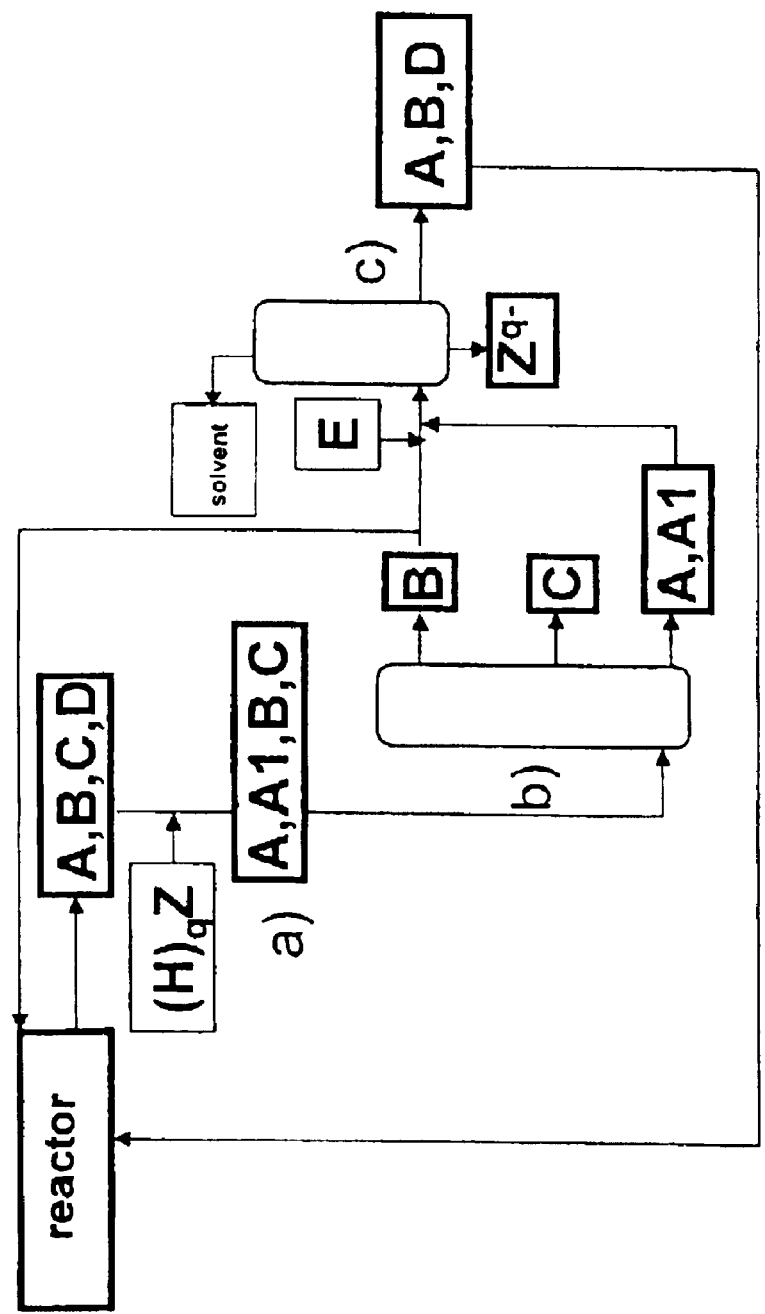
FIG. 5 shows a block diagram of the steps in an embodiment of the process of the present invention.

FIG. 5 describes a process in which B2 is identical to B and the acid is added as such or in a solvent. Step b) is performed by fractional distillation, step c) by reactive distillation. A1 and B are reacted with E to give D and held in solution with excess B. When aqueous E has been added, a solvent/water azeotrope, for example, is distilled off. As a result of the solubility then becoming poorer, $Z^{q-}$ precipitates out with the gegenion and may be separated. The mixture obtained at the base of the column which contains A, B and D is recycled to the reaction.

An example of this type of procedure is e.g. the use of $CO_2$ or tetraalkylammonium hydrogen carbonate as $(H)_qZ$. When neutralising tetraalkylammonium phenolate (D), tetraalkylammonium carbonate (A1) is produced and is supplied to the reactive distillation. A suspension of calcium hydroxide is used as base (E). Calcium carbonate then precipitates out ($Z^{q-}$=carbonate). The water is distilled off, with the solvent as an azeotroping agent, wherein excess $Ca(OH)_2$ precipitates out. The solids are filtered off and the mixture at the base of the distillation column is reused. The use of inexpensive reagents (carbon dioxide, which is produced as a secondary product, e.g. during the direct carbonylation of phenol, and calcium hydroxide) makes this variant interesting.

Figure 6:
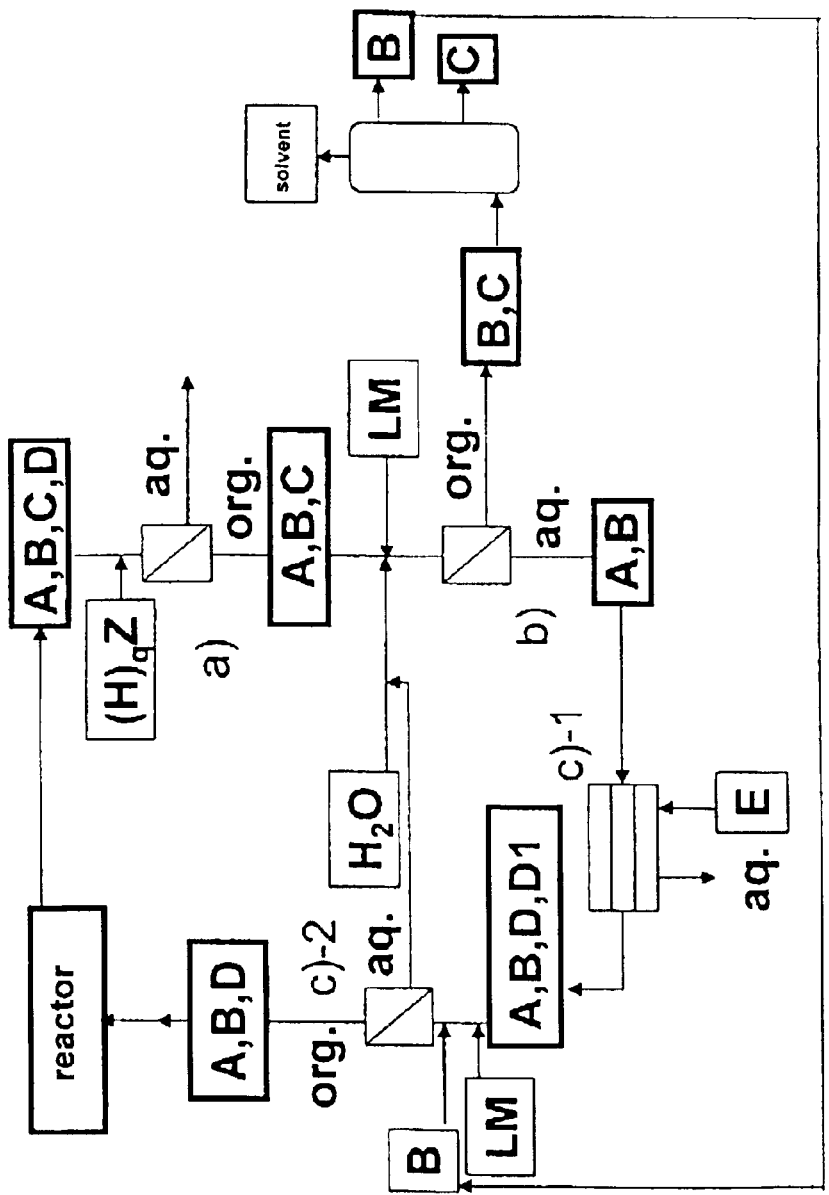
FIG. 6 shows a block diagram of the steps in an embodiment of the process of the present invention.

In the variant shown in FIG. 6, A1 and A, and B2 and B, are each identical. The mixture of A, B, C and D emerging from the reactor is again extracted in step a) with an aqueous acid solution $(H)_qZ$, wherein D reacts to give B and A. In step b), the mixture to which solvent and water have been added is extracted, wherein an aqueous phase consisting of A and B, and an organic phase consisting of solvent (LM), B and C are produced. The organic phase is worked-up by distillation to recover the solvent, product C and B. The B obtained may be used again in the reaction or during the working-up procedure.

The aqueous phase is reacted in step c)-1 in an ion-exchanger loaded with base E. A and D are produced. Depending on the concentration of B in this stream, B may also be present in the stream at the exit from the ion-exchanger. If there are very low concentrations of B, then a base D1 may also be produced. For example, if the ion-exchanger is loaded with NaOH, a quaternary hydroxide (D1) is produced in addition to the quaternary phenolate (D). Solvent and B are now added to the aqueous stream at the exit from the ion-exchanger, which contains A, B, D and optionally D1, wherein step c)-2, i.e. optional conversion of D1 to D, proceeds. The mixture is extracted, the phases are separated, the organic phase which contains A, B and D is recycled to the reactor, optionally after further working-up. The aqueous phase may again be fed to extraction b), and thus circulated.

As shown in FIGS. 1 to 6, solvent (LM) and B are used in different concentrations at various points when performing the process according to the invention. To a person skilled in the art, different variants of the process are obvious in which streams of LM and/or B are produced, which may be adjusted to the required concentration by appropriate separating, concentrating and mixing operations, and may be incorporated in a suitable manner within the overall process in order to produce the mixtures required for the individual extraction steps.

A person skilled in the art also knows that the process depends on the chemical nature of the species A, B, C and D and of the solvent LM and that, depending on the partition coefficient and separation performance required for the individual extractions a2), b1) or d1), a suitable number of theoretical separating steps has to be involved for the specific separating problem being considered.

EXAMPLES

The extractions are performed by shaking the phases for approximately half an hour. Then the organic and aqueous phases are tested, after dilution with acetone and biphenyl as internal standards, using gas chromatography in order to determine the concentrations of the components. Tetrabutylammonium bromide (TBAB) decomposes to give tributylamine (TBA) and butyl bromide, which are detected. (Tetrabutylammonium bromide=TBAB, monochlorobenzene=MCB, diphenylcarbonate=DPC).

Example 1

5432 g of the reaction solution from an oxidative direct carbonylation process are extracted at 80° C. with a solution of 33 ml of 48% HBr in 543 g of water. 556.2 g of aqueous extract are obtained. The compositions of the solutions after a single extraction step are given in table 1.

TABLE 1

|  | Mn [ppm] | Phenol [wt. %] | TBA [wt. %] | TBAB [wt. %] | TBAP [wt. %] | DPC [wt. %] |
|---|---|---|---|---|---|---|
| Reaction mixture | 250 | 5.26 | 2.71 | 2.12 | 1.12 | 13.33 |
| Organic phase | <5 | 5.29 | 2.92 | 3.98 | 0 | 13.27 |
| Aqueous phase | 2700 | 0.64 | 0.01 | 0.01 | 0 | 0 |

Example 2

200 g of a solution with the approximate composition 4 wt. % tetrabutylammonium bromide, 4 wt. % tetrabutylammonium phenolate, 6 wt. % phenol, 20 wt. % DPC and 66 wt. % chlorobenzene are extracted at 80° C. with 3 portions of the same volume of a solution of 0.93 g HBr in 599.07 g of water. The aqueous phases are then combined. The compositions of the solutions are given in table 2.

Comparison Example 2

200 g of the solution used in example 2 are extracted at 80° C. 3 times with 3 portions of the same volume of a total of 600 g of water. The aqueous phases are then combined. The compositions of the solutions are given in table 2.

TABLE 2

|  | Example 2 | | | Comparison 2 | | |
|---|---|---|---|---|---|---|
|  | Phenol [g] | TBA [g] | DPC [g] | Phenol [g] | TBA [g] | DPC [g] |
| Organic phase | 2.71 | 0.16 | 19.77 | 5.54 | 0.70 | 16.01 |
| Aqueous phases | 3.25 | 3.75 | 0.04 | 3.33 | 3.33 | 0.02 |

Example 3

A mixture of 50 g of tetraphenylphosphonium bromide, 60 g of chlorobenzene, 40 g of phenol and 100 g of diphenyl carbonate is distilled over a 5 cm high column filled with Raschig rings. Initially the system is operated under a vacuum of 200 mbar until the temperature at the base of the column has risen to about 180° C., then the vacuum is reduced to about 20 mbar and distillation is continued up to a maximum temperature at the base of the column of about 200° C. The total amount of compounds found in the distillate is calculated by adding up the compositions of the individual fractions. 69.1 g of material from the reaction remain at the base of the column. The results are given in table 3.

Comparison Example 3

A mixture of 25 g tetraphenylphosphonium bromide, 25 g tetraphenylphosphonium phenolate, 60 g chlorobenzene, 40 g phenol and 100 g diphenyl carbonate is distilled over a 5 cm high column filled with Raschig rings. Initially the system is operated under a vacuum of 200 mbar until the temperature at the base of the column has risen to about 180° C., then the vacuum is reduced to about 20 mbar and distillation is continued up to a maximum temperature at the base of the column of about 200° C. The total amount of compounds found in the distillate is calculated by adding up the compositions of the individual fractions. 66.7 g of material from the reaction remain at the base of the column. The results are given in table 3.

TABLE 3

|  | Ex. 3 | | Comp. 3 | |
|---|---|---|---|---|
|  | Phenol [g] | DPC [g] | Phenol [g] | DPC [g] |
| Distillate | 39.0 | 77.9 | 56.5 | 61.6 |

Example 4

61.8 g of a 95.4% strength sulfuric acid are carefully added dropwise to a solution of 50 g KBr in 150 g water. The mixture which results is distilled at atmospheric pressure. 120 ml of first runnings are obtained, the remaining fractions are combined and produce 113.7 g of a 25.74% strength HBr solution.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the removal and recovery of quaternary salt (A) and base (D) from a reaction mixture that contains in addition to (A) and (D), at least one hydroxyaromatic compound (B) and at least one reaction product (C) and optionally a solvent, comprising a) adding acid to the reaction mixture to cause conversion of (D) into a hydroxyaromatic compound (B2)

b) separating the reaction mixture into b1) that contains (C), a portion of (B2), and optionally (B) and b2 that contains (A), a portion of (B2), and optionally (B), wherein the separation is performed by a method selected from distillation, extraction, cascades and combinations thereof, and c) reacting b1 and b2) with a base (E) to re-form (D)

where (A) conforms to $(Q^{n+})_m(Y^{m-})_n$, and (D) conforms to $(W^{l+})_k[(^-O)_k Ar']_l$, wherein n, m, k and l independently one of the others represent integers, Ar' represents an aromatic group, $Q^{n+}$ denotes a hexaalkylguanidinium ion or $XR_r^+)_n$, wherein X denotes an atom selected from group consisting of group Va and group VIa of the Periodic Table of the elements, r is an integer of 1 to 4, n is an integer of 1 to 10, and R independently represent $C_1$–$C_{18}$-alkyl, $C_1$–$C_{18}$-cycloalkyl, $C_7$–$C_{18}$-aralkyl or $C_6$–$C_{18}$-aryl with the proviso that a pair of substituents radicals may be replaced by a ring system, $Y^{m-}$ is at least one member selected from the group consisting of halides, nitrate, sulfate, hydrogen sulfate, carbonate, hydrogen carbonate, phosphate, hydrogen phosphate, dihydrogen phosphate, tetrafluoroborate, perchlorate, carboxylates and hexafluorophosphates and m is an integer of 1 to 3, $W^{l+}$ is at least one member selected from the group consisting of alkali metal, alkaline earth metal, rare earth metal, transition metal and quaternary cations $Q^{n+}$, (B) and (B2) independently correspond to the formula $Ar(OH)_p$, wherein Ar represents a aromatic group and p is an integer from 1 to 4, (E) is one or more hydroxide of a member selected from the group consisting of alkaline earth metal, alkali metal, ammonium and $Q^{n+}$ and wherein acid is at least one member selected from the group consisting of hydrobromic acid, hydrochloric acid, carbon dioxide, phosphoric acid, dihydrogen phosphate, nitric acid, formic acid, acetic acid, oxalic acid, hydrogen sulfate and sulfuric acid.

2. The process according to claim 1, in which B and B2 are identical.

3. The process according to claim 1, in which C contains a diaryl carbonate.

4. The process according to claim 1, wherein reaction product contains a solvent that is at least one member selected from the group consisting of halogenated hydrocarbons, dialkylethers, chlorobenzene, dichlorobenzene, fluorobenzene, benzene, anisol, methylene chloride, 1,2-dichloroethane, dioxan, tetrahydrofuran, t-butyl methyl ether and etherified glycols.

5. The process according to claim 1, wherein reaction product contains an aromatic solvent.

6. The process according to claim 1, in which the acid is added as an aqueous solution.

7. The process according to claim 1, in which step a) is performed by reactive extraction.

8. The process according to claim 1, in which step c) is performed by reactive extraction and/or by reactive distillation.

* * * * *